(12) United States Patent
Guo et al.

(10) Patent No.: US 8,338,438 B2
(45) Date of Patent: Dec. 25, 2012

(54) POLYMORPH FORMS OF 4-ANILINOQUINAZOLINE DERIVATIVES, THE PREPARATION METHODS AND USES THEREOF

(75) Inventors: Jianhui Guo, Shanghai (CN); Yong Jiang, Shanghai (CN)

(73) Assignee: Shanghai Allist Pharmaceuticals, Inc. (CN)

( * ) Notice: Subject to any disclaimer, the term of this patent is extended or adjusted under 35 U.S.C. 154(b) by 0 days.

(21) Appl. No.: 12/934,478

(22) PCT Filed: Mar. 25, 2009

(86) PCT No.: PCT/CN2009/000317
§ 371 (c)(1),
(2), (4) Date: Oct. 26, 2010

(87) PCT Pub. No.: WO2009/117899
PCT Pub. Date: Oct. 1, 2009

(65) Prior Publication Data
US 2012/0004249 A1   Jan. 5, 2012

(30) Foreign Application Priority Data

Mar. 25, 2008   (CN) .......................... 2008 1 0043189

(51) Int. Cl.
*A01N 43/54* (2006.01)
*A61K 31/517* (2006.01)
*C07D 239/72* (2006.01)

(52) U.S. Cl. .................................. 514/266.1; 544/283
(58) Field of Classification Search ............... 514/266.1; 544/283
See application file for complete search history.

(56) References Cited

FOREIGN PATENT DOCUMENTS

| WO | WO96/30347 A1 | 10/1996 |
| WO | WO96/33980 A1 | 10/1996 |
| WO | WO99/06378 A1 | 2/1999 |
| WO | WO00/06555 A1 | 2/2000 |
| WO | WO00/31048 A1 | 6/2000 |
| WO | WO2006/071017 | 7/2006 |
| WO | WO2007/082434 | * 7/2007 |
| WO | WO2008/098485 | * 8/2008 |

OTHER PUBLICATIONS

Pinedo et al.*
McMahon et al.*
International Search Report and Written Opinion of corresponding PCT application No. PCT/CN2009/000317, date of mailing Jul. 2, 2009.
Supplementary European Search Report corresponding to European Application No. 09724386 dated Feb. 17, 2011.

* cited by examiner

*Primary Examiner* — Paul V. Ward

(57) ABSTRACT

The present invention relates to polymorphic forms of N-{4-[3-chloro-4-(3-fluoro-benzyloxy)phenylamino]-quinazolin-6-yl}-acrylamide p-toluenesulfonate with the characteristic X-ray powder diffraction data as stated in the description, preparation methods thereof, pharmaceutical compositions comprising the same and the use thereof.

12 Claims, 7 Drawing Sheets

POLYMORPH FORMS OF 4-ANILINOQUINAZOLINE DERIVATIVES, THE PREPARATION METHODS AND USES THEREOF

CROSS REFERENCE TO RELATED APPLICATIONS

This application is a 35 U.S.C. §371 national phase application of PCT Application No. PCT/CN2009/000317, filed on Mar. 25, 2009, which claims priority from Chinese Patent Application 200810043189.7, filed on Mar. 25, 2008, the disclosures and contents of which are incorporated by reference herein in their entirety. The above-referenced PCT International Application was published in Chinese as International Publication No. WO2009/117899.

FIELD OF THE INVENTION

The present invention relates to the polymorphic forms of 4-phenylamino quinazoline derivatives. Specifically, the present invention relates to the polymorphic forms of p-Toluenesulfonate salt of the compound of formula (I) (the chemical name is N-{4-[3-chloro-4-(3-fluoro-benzyloxy)phenylamino]-quinazolin-6-yl}-acrylamide), their preparation methods, pharmaceutical compositions comprising said polymorphic forms and their use.

BACKGROUND OF THE INVENTION

Protein tyrosine kinase (PTK) is a type of enzyme which plays an important role in normal cell growth. Protein tyrosine kinases catalyze the transfer of phosphate groups from ATP to the residues of the protein substrate. Many epidermal growth factor receptors (EGFR) have the effect of PTK, and the interaction of these receptors and growth factors is necessary in normal cell growth regulation. However, the overexpression of EGFR may cause excessive cell proliferation by the tyrosine kinase action of its own, and finally lead to the formation of tumors.

The epidermal growth factor receptor family can be divided into EGFR (Erb-B1), Erb-B2 (HER-2/neu), Erb-B3 and Erb-B4 according to structure. All of these epidermal growth factor receptors have been already confirmed to be related to most cancers.

Due to the important effect of the abnormal receptor kinases on the pathogenesis of cancer, the recent researches on anti-cancer agents focus on the development of the specific PTK inhibitors as potential anti-cancer therapeutic agents. The research of quinazoline derivatives as PTK inhibitors for further application to cancer treatment arouses wide attraction.

WO 96/30347 (Chinese patent application CN 96102992) and WO 96/33980 relate to some 4-(substituted-phenylamino)-quinazoline derivatives, their prodrugs, their pharmaceutically acceptable salts and their use in treating diseases caused by excessive cell proliferation.

WO 99/06378, WO 2000/31048 and WO 2000/06555 (Chinese patent application CN 99808949) also relate to substituted quinazoline derivatives having irreversible PTK inhibitory activity.

WO 2006/071017 mentions some quinazoline derivatives that inhibit growth of cancer cells.

WO 2007/082434 describes a novel type of 4-phenylamino quinazoline derivatives and their use as PTK inhibitors, wherein, it is proven by experiments that the compound N-{4-[3-chloro-4-(3-fluoro-benzyloxy)phenylamino]-quinazolin-6-yl}-acrylamide prepared in Example 8 possesses the relatively good effect of inhibiting the growth of human epidermoid squamous cancer cell A431 and human breast cancer cell BT-474. The compound also possesses the significant tumor-inhibiting effect on human epidermoid squamous cancer cell A431 implanted into a nude mouse. It is also proven by in vitro experiments that the compound has excellent inhibitory activity against Erb-B2 kinase.

A crystalline form has some influence on the physical properties of compounds. Because of different crystal lattice structures, pharmaceutical compounds with many kinds of crystalline forms may have not only different appearances (color and shape such as needle-shaped crystal, crystalline lamellar and crystalline granule), but also different physical properties (such as melting point, solubility, density, stability and hygroscopicity), resulting in that they show different dissolution and absorption behaviors in vivo, and this might have influence on the clinical effect and safety of the pharmaceutical compounds to a certain extent.

Specific crystalline form will have different thermodynamic behaviors as compared to amorphous state or another crystalline form. Melting point apparatus, thermogravimetric analysis (TGA) or Differential Scanning Clorimetry (DSC) and the like can be used in laboratories to measure the thermal properties to differentiate a certain specific crystalline form, amorphous state and another crystalline form. Specific crystalline forms may have special spectral properties. For example, the data of both X-ray powder diffraction pattern and IR spectra can characterize specific crystalline forms.

The above-mentioned documents are hereby fully incorporated in this disclosure by reference herein.

CONTENTS OF THE INVENTION

The present invention provides novel polymorphic forms of N-{4-[3-chloro-4-(3-fluoro-benzyloxy)phenylamino]-quinazolin-6-yl}-acrylamide (as defined in formula (I) below) p-Toluenesulfonate, their preparation methods, pharmaceutical compositions comprising said polymorphic forms and their use in the manufacture of a medicament for the treatment and/or prevention of tumors and the method of treatment and/or prevention of tumors in a mammal.

In summary, the present invention provides the technical solutions as follows:

1. The crystalline p-Toluenesulfonate salt of the compound N-{4-[3-chloro-4-(3-fluoro-benzyloxy)phenylamino]-quinazolin-6-yl}-acrylamide as shown by formula (I):

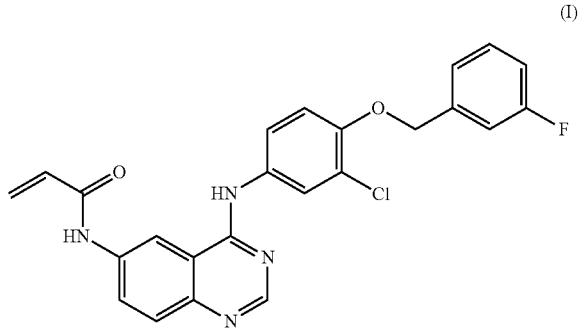

(I)

2. Crystalline form A of the N-{4-[3-chloro-4-(3-fluoro-benzyloxy)phenylamino]-quinazolin-6-yl}-acrylamide p-Toluenesulfonate salt, i.e., Form A, characterized in that the X-ray powder diffraction pattern has peaks at the diffraction angle 2θ(°) of 5.92±0.10, 8.64±0.10, 11.86±0.10, 16.58±0.10, 16.94±0.10, 17.86±0.10, 19.12±0.10, 19.66±0.10, 20.12±0.10, 23.42±0.10, 24.14±0.10, 24.80±0.10, and 26.76±0.10.

3. Form A according to the technical solution 2, characterized in that the X-ray powder diffraction pattern provided by said Form A also contains peaks at the diffraction angle 2θ(°) of 9.80±0.10, 13.28±0.10, 14.78±0.10, 17.36±0.10, 18.62±0.10, 21.62±0.10, 22.12±0.10, 22.38±0.10, 23.14±0.10, 25.20±0.10, 27.24±0.10, 28.34±0.10, 28.78±0.10, 33.12±0.10, and 41.70±0.10.

4. Form A according to the technical solution 2 or 3, characterized in that said Form A has the X-ray powder diffraction pattern as substantially shown in FIG. 1.

5. Form A according to the technical solution 4, characterized in that said Form A also has the IR spectrum as substantially shown in FIG. 5.

6. A process for preparing Form A according to any one of the technical solutions 2-5, comprising the steps of:
(a) dissolving the compound as shown in the following formula (I) in an organic solvent to form a solution;

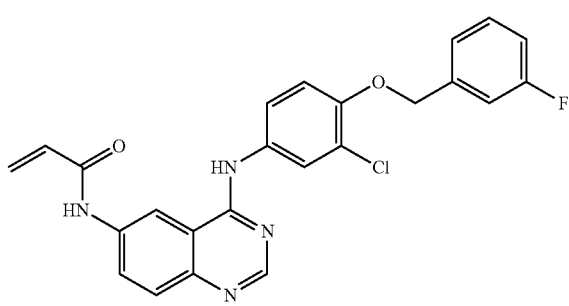

(b) adding dropwise a solution formed from p-Toluenesulfonic acid in said organic solvent under stirring and controlling the molar ratio of the compound of formula (I) to p-Toluenesulfonic acid in the range of 1:1~6, preferably 1:3~6; and
(c) resulting in a crystalline precipitate, and filtering out and washing the crystal to obtain the target crystal.

7. A process according to the technical solution 6, characterized in that the organic solvent is selected from the group consisting of tetrahydrofuran, methanol, ethanol, propanol, isopropanol, butanol, acetone, acetonitrile, DMSO, DMF, propanediol and the mixtures thereof, preferably consisting of tetrahydrofuran, methanol, ethanol, the mixture of tetrahydrofuran and methanol, and the mixture of tetrahydrofuran and ethanol.

8. A process according to the technical solution 7, wherein the organic solvent is the mixture of tetrahydrofuran and methanol with a volume ratio of 1:1~3, preferably 1:2~3.

9. A process according to any one of the technical solutions 6-8, characterized in that the solution of the compound of formula (I) in the step (a) has a concentration of 3~8 g/100 mL, preferably 4~6 g/100 mL.

10. A process according to any one of the technical solutions 6-9, characterized in that the solution of p-Toluenesulfonic acid in the step (b) has a concentration of 10~30 g/100 mL, preferably 15~25 g/100 mL.

11. Crystalline form B of the N-{4-[3-chloro-4-(3-fluoro-benzyloxy)phenylamino]-quinazolin-6-yl}-acrylamide p-Toluenesulfonate salt, i.e., Form B, characterized in that the X-ray powder diffraction pattern has peaks at the diffraction angle 2θ(°) of 4.72±0.10, 17.04±0.10, 19.32±0.10, and 24.12±0.10.

12. Form B according to the technical solution 11, characterized in that the X-ray powder diffraction pattern also has peaks at the diffraction angle 2θ(°) of 7.92±0.10, 9.54±0.10, 11.90±0.10, 12.94±0.10, 14.34±0.10, 15.32±0.10, 17.88±0.10, 20.00±0.10, 21.80±0.10, 22.42±0.10, 25.08±0.10, 25.80±0.10, 27.28±0.10, 28.00±0.10, and 28.44±0.10.

13. Form B according to the technical solution 11 or 12, characterized in that said Form B has the X-ray powder diffraction pattern as substantially shown in FIG. 2.

14. Form B according to the technical solution 13, characterized in that said Form B also has the IR spectrum as substantially shown in FIG. 6.

15. A process for preparing Form B according to any one of the technical solutions 11-14, comprising the steps of:
(a) dissolving the crystalline form A of N-{4-[3-chloro-4-(3-fluoro-benzyloxy)phenylamino]-quinazolin-6-yl}-acrylamide p-Toluenesulfonate according to any one of the technical solutions 2-5 in the mixture of a protic solvent and an aprotic solvent by heating to form a solution;
(b) maintaining the solution for 1~2 h at the temperature of 40~80° C.;
(c) cooling the solution and resulting in a crystalline precipitate, letting the resulting mixture stand, filtering out and washing the crystal to obtain the target crystal.

16. A process according to the technical solution 15, wherein the protic solvent is water or the mixture of water and an alcohol.

17. A process of the technical solution 15 or 16, wherein the aprotic solvent is selected from the group consisting of tetrahydrofuran, ether, dichloromethane, acetone, acetonitrile, DMF, and the mixtures thereof.

18. A process according to any one of the technical solutions 15-17, wherein the solution of the crystalline form A of the N-{4-[3-chloro-4-(3-fluoro-benzyloxy)phenylamino]-quinazolin-6-yl}-acrylamide p-Toluenesulfonate in the step (a) has a concentration of 2~10 g/100 mL, preferably 4~8 g/100 mL.

19. A process according to any one of the technical solutions 15-18, characterized in that the volume ratio of the protic solvent to the aprotic solvent in the mixture of a protic solvent and an aprotic solvent is 1:2~4, preferably 1:3~4.

20. Crystalline form C of the N-{4-[3-chloro-4-(3-fluoro-benzyloxy)phenylamino]-quinazolin-6-yl}-acrylamide p-Toluenesulfonate salt, i.e., Form C, characterized in that the X-ray powder diffraction pattern has peaks at the diffraction angle 2θ(°) of 3.40±0.10, 6.82±0.10, 7.58±0.10, 11.30±0.10, 14.84±0.10, 15.24±0.10, 17.28±0.10, 17.86±0.10, 18.34±0.10, 20.32±0.10, 22.96±0.10, 23.50±0.10, 24.12±0.10, 24.62±0.10, and 25.86±0.10.

21. Form C according to the technical solution 20, characterized in that the X-ray powder diffraction pattern also has peaks at the diffraction angle 2θ(°) of 9.04±0.10, 10.26±0.10, 22.44±0.10, 25.06±0.10, 26.98±0.10, 28.62±0.10, and 29.98±0.10.

22. Form C according to the technical solution 20 or 21, characterized in that said Form C has the X-ray powder diffraction pattern as substantially shown in FIG. 3.

23. Form C according to the technical solution 22, characterized in that said Form C also has the IR spectrum as substantially shown in FIG. 7.

24. A process for preparing Form C according to any one of the technical solutions 20-23, comprising the steps of:

(a) dissolving the crystalline form A of N-{4-[3-chloro-4-(3-fluoro-benzyloxy)phenylamino]-quinazolin-6-yl}-acrylamide p-Toluenesulfonate according to any one of the technical solutions 2-5 in the mixture of a protic solvent and an aprotic solvent;
(b) adding dropwise a solution formed from p-Toluenesulfonic acid in said mixture of a protic solvent and an aprotic solvent under stirring and controlling the molar ratio of said Form A to p-Toluenesulfonic acid in the range of 1:1~6, preferably 1:3~6; and
(c) resulting in a crystalline precipitate, letting the resulting mixture stand, and filtering out and washing the crystal to obtain the target crystal.
25. A process according to the technical solution 24, wherein the protic solvent is water or the mixture of water and an alcohol.
26. A process of the technical solution 24 or 25, wherein the aprotic solvent is selected from the group consisting of tetrahydrofuran, ether, dichloromethane, acetone, acetonitrile, DMF, and the mixtures thereof.
27. A process according to any one of the technical solutions 24-26, wherein the solution of the crystalline form A of the N-{4-[3-chloro-4-(3-fluoro-benzyloxy)phenylamino]-quinazolin-6-yl}-acrylamide p-Toluenesulfonate in the step (a) has a concentration of 3~7 g/100 mL, preferably 4~6 g/100 mL.
28. A process according to any one of the technical solutions 24-27, wherein the solution of p-Toluenesulfonic acid in the step (b) has a concentration of 10~30 g/100 mL, preferably 15~25 g/100 mL.
29. A process of any one of the technical solutions 24-28, characterized in that the volume ratio of the protic solvent to the aprotic solvent in said mixture of a protic solvent and an aprotic solvent is 1:1~5, preferably 1:3~4.
30. A pharmaceutical composition comprising the crystalline form according to any one of the technical solutions 1-5, 11-14 and 20-23 and a pharmaceutically acceptable carrier.
31. A pharmaceutical composition of the technical solution 30, which further comprises one or more additional drugs for the treatment and/or prevention of tumors.
32. Use of the crystalline form according to any one of the technical solutions 1-5, 11-14 and 20-23 in the preparation of a medicament for the treatment and/or prevention of tumors.
33. A method for treating and/or preventing tumors in a mammal, comprising the administration of the crystalline form according to any one of the technical solutions 1-5, 11-14 and 20-23 in an amount effective in treatment and/or prevention to a mammal in need.
34. The use of the technical solution 32 or the method of the technical solution 33, wherein the tumor is selected from the group consisting of breast cancer, non-small cell lung cancer, ovarian cancer, gastric cancer, colonic cancer, pancreatic cancer and epidermatoid squamous cancer.

Specifically, in accordance with the first aspect of the present invention, there is provided the crystal of p-Toluenesulfonate salt of compound of formula (I), and also provided three polymorphic forms of p-Toluenesulfonate salt of compound of formula (I), respectively named as Form A, Form B and Form C.

Firstly, the present invention provides a crystal with the X-ray powder diffraction pattern containing high intensity peaks at the diffraction angle 2θ(°) of 5.92±0.10, 8.64±0.10, 11.86±0.10, 16.58±0.10, 16.94±0.10, 17.86±0.10, 19.12±0.10, 19.66±0.10, 20.12±0.10, 23.42±0.10, 24.14±0.10, 24.80±0.10, and 26.76±0.10, and it is defined as Form A in the present application.

In addition to the characteristic high strength diffraction peaks as mentioned above, the X-ray powder diffraction pattern of said Form A also contains intermediate strength peaks at the diffraction angle 2θ(°) of 9.80±0.10, 13.28±0.10, 14.78±0.10, 17.36±0.10, 18.62±0.10, 21.62±0.10, 22.12±0.10, 22.38±0.10, 23.14±0.10, 25.20±0.10, 27.24±0.10, 28.34±0.10, 28.78±0.10, 33.12±0.10, and 41.70±0.10.

The X-ray powder diffraction pattern of said Form A is substantially shown in FIG. 1. The relative strength of each peak is described in the following table:

| 2θ(°) | I/I₀ | 2θ(°) | I/I₀ | 2θ(°) | I/I₀ | 2θ(°) | I/I₀ |
|---|---|---|---|---|---|---|---|
| 5.92 | vs | 8.64 | vs | 9.80 | m | 10.24 | w |
| 11.86 | s | 13.28 | m | 14.78 | m | 15.36 | w |
| 16.58 | vs | 16.94 | s | 17.36 | m | 17.86 | s |
| 18.62 | m | 19.12 | s | 19.66 | s | 20.12 | vs |
| 21.62 | m | 22.12 | m | 22.38 | m | 23.14 | m |
| 23.42 | s | 24.14 | s | 24.80 | s | 25.20 | m |
| 25.90 | w | 26.76 | s | 27.24 | m | 28.34 | m |
| 28.78 | m | 30.14 | w | 32.06 | w | 33.12 | m |
| 34.94 | w | 37.58 | w | 38.94 | w | 41.70 | m |
| 42.74 | w | 44.22 | w | | | | |

Form A also has the IR spectrum as substantially shown in FIG. 5.

Form A is yellow-green crystalline powder, with a melting point of 245° C.

In addition, the present invention also provides another crystal with the X-ray powder diffraction pattern containing high strength peaks at the diffraction angle 2θ(°) of 4.72±0.10, 17.04±0.10, 19.32±0.10, and 24.12±0.10, and it is defined as Form B in the present application.

In addition to the characteristic high intensity diffraction peaks as mentioned above, the X-ray powder diffraction pattern of said Form B also contains intermediate intensity peaks at the diffraction angle 2θ(°) of 7.92±0.10, 9.54±0.10, 11.90±0.10, 12.94±0.10, 14.34±0.10, 15.32±0.10, 17.88±0.10, 20.00±0.10, 21.80±0.10, 22.42±0.10, 25.08±0.10, 25.80±0.10, 27.28±0.10, 28.00±0.10, and 28.44±0.10.

The X-ray powder diffraction pattern of Form B is substantially shown in FIG. 2. The relative intensity of each peak is described in the following table:

| 2θ(°) | I/I₀ | 2θ(°) | I/I₀ | 2θ(°) | I/I₀ | 2θ(°) | I/I₀ |
|---|---|---|---|---|---|---|---|
| 4.72 | vs | 7.92 | m | 8.46 | w | 9.54 | m |
| 11.90 | m | 12.26 | w | 12.94 | m | 14.34 | m |
| 15.32 | m | 17.04 | s | 17.88 | m | 18.50 | w |
| 19.32 | s | 20.00 | m | 20.56 | w | 21.80 | m |
| 22.42 | m | 24.12 | s | 25.08 | m | 25.80 | m |
| 26.80 | w | 27.28 | m | 28.00 | m | 28.44 | m |
| 29.50 | w | 30.22 | w | 31.54 | w | 42.30 | w |
| 44.54 | w | | | | | | |

Form B also has the IR spectrum as substantially shown in FIG. 6.

Form B is a pale yellow crystalline powder, with a melting point of 235.4° C.

In addition, the present invention also provides a crystal with the X-ray powder diffraction pattern containing the high intensity peaks at the diffraction angle 2θ(°) of 3.40±0.10, 6.82±0.10, 7.58±0.10, 11.30±0.10, 14.84±0.10, 15.24±0.10, 17.28±0.10, 17.86±0.10, 18.34±0.10, 20.32±0.10, 22.96±0.10, 23.50±0.10, 24.12±0.10, 24.62±0.10, and 25.86±0.10, and it is defined as Form C in the present application.

In addition to the characteristic high intensity diffraction peaks as mentioned above, the X-ray powder diffraction pattern of said Form C also contains middle intensity peaks at the diffraction angle 2θ(°) of 9.04±0.10, 10.26±0.10, 22.44±0.10, 25.06±0.10, 26.98±0.10, 28.62±0.10, and 29.98±0.10.

The X-ray powder diffraction pattern of Form C is substantially shown in FIG. 3. The relative intensity of each peak is described in the following table:

| 2θ(°) | I/I₀ | 2θ(°) | I/I₀ | 2θ(°) | I/I₀ | 2θ(°) | I/I₀ |
|---|---|---|---|---|---|---|---|
| 3.40 | vs | 4.80 | w | 6.82 | vs | 7.58 | vs |
| 9.04 | m | 10.26 | m | 11.30 | s | 12.44 | w |
| 12.90 | w | 14.04 | w | 14.84 | s | 15.24 | s |
| 17.28 | vs | 17.86 | vs | 18.34 | s | 19.05 | w |
| 20.32 | s | 21.36 | w | 22.44 | m | 22.96 | s |
| 23.50 | s | 24.12 | s | 24.62 | vs | 25.06 | m |
| 25.86 | vs | 26.98 | m | 28.62 | m | 29.98 | m |
| 31.44 | w | 33.02 | w | 34.44 | w | 37.02 | w |
| 37.80 | w | 38.84 | w | 44.35 | w | 46.68 | w |

Form C also has the IR spectrum as substantially shown in FIG. 7.

Form C is a yellow crystalline powder, with a melting point of 244° C.

In present invention, the powder X-ray diffraction patterns of the three types of crystals mentioned above were obtained by known methods in the art with RIGAKUD/MNX2550VB/PC X ray diffractometer.

In the powder X-ray diffraction pattern, each peak was identified by Bragg formula calculation, and the site of each peak was determined by the diffraction angle 2θ(°). The division of the intensity of peak only reflects the similar size of peaks in each site. In the present invention, each crystalline form took the highest diffraction peak of its peak height as the base peak which was defined as $I_0$, with the relative intensity as 100% (for example, the peak at 2θ(°) of 5.92 in FIG. 1 as the base peak of Form A, the peak at 2θ(°) of 4.72 in FIG. 2 as the base peak of Form B, the peak at 2θ(°) of 25.86 in FIG. 3 as the base peak of Form C). Other peaks had the ratio of their height to the height of the base peak as relative intensity $I/I_0$. The definition of relative intensity of each peak was shown in the following table:

| Relative intensity I/I₀ (%) | Definition |
|---|---|
| 50~100 | Vs (very strong) |
| 20~50 | S (strong) |
| 5~20 | M (medium) |
| 1~5 | W (weak) |

The IR spectra of the three crystals mentioned above were measured by the known method in the art, using Shimazu FTIR-8400S infrared spectrophotometer in the mode of KBr pelleting. The melting points of the crystals mentioned above were measured by the known method in the art, using WRS-2A/2 microcomputer melting point instrument.

Because of error of instrument or the difference of operators, one skilled in the art can understand the slight difference in the parameters which characterize physical properties of crystals. Therefore, the parameters mentioned above only aid to characterize the polymorphs provided in the present invention, not regarded as the limitations to the polymorphs provided in the present invention.

In accordance with the second aspect of the present invention, there is provided a process for preparing the three polymorphic forms of the present invention.

Firstly, the present invention provides a process for preparing Form A, comprising the steps of:
(a) dissolving the compound of formula (I) in an organic solvent to form a solution;

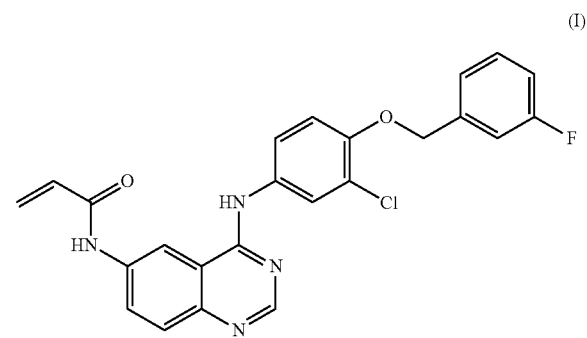

(I)

(b) adding dropwise a solution formed from p-Toluenesulfonic acid in said organic solvent under stirring and controlling the molar ratio of the compound of formula (I) to p-Toluenesulfonic acid in the range of 1:1~6, preferably 1:3~6;
(c) resulting in a crystalline precipitate, and filtering out and washing the crystal to obtain the target crystal, the crystalline form A of N-{4-[3-chloro-4-(3-fluoro-benzyloxy)phenylamino]-quinazolin-6-yl}-acrylamide p-Toluenesulfonate salt.

The organic solvent mentioned above is selected from the group consisting of tetrahydrofuran, methanol, ethanol, propanol, isopropanol, butanol, acetone, acetonitrile, DMSO, DMF, propanediol and the mixtures thereof, preferably consisting of tetrahydrofuran, methanol, ethanol, the mixture of tetrahydrofuran and methanol, the mixture of tetrahydrofuran and ethanol, especially the mixture of tetrahydrofuran and methanol. The volume ratio of tetrahydrofuran to methanol in the mixture has a certain effect on the crystallization, and a preferred volume ratio is 1:1~3, particularly 1:2~3.

The solution of the compound of formula (I) in the above step (a) has a concentration of 3~8 g/100 mL, preferably 4~6 g/100 mL.

The solution of p-Toluenesulfonic acid in the above step (b) has a concentration of 10~30 g/100 mL, preferably 15~25 g/100 mL.

Generally, the above preparation process is carried out under the condition of cooling, room temperature or heating. It is noteworthy that the selection of reaction temperature has some effect on the formation of different crystals, which is also known by one skilled in the art. The crystallization temperature used in present invention is between −10° C. to the boiling point of the solvent as used, preferably 0~40° C.

In addition, the present invention provides a process for preparing the Form B, comprising the steps of:
(a) dissolving the above crystalline form A of the N-{4-[3-chloro-4-(3-fluoro-benzyloxy)phenylamino]-quinazolin-6-yl}-acrylamide p-Toluenesulfonate in the mixture of a protic solvent and an aprotic solvent by heating to form a solution;
(b) maintaining the solution for 1~2 h at the temperature of 40~80° C.;

(c) cooling the solution and resulting in a crystalline precipitate, letting the resulting mixture stand, and filtering out and washing the crystal to obtain the target crystal, the crystalline form B of N-{4-[3-chloro-4-(3-fluoro-benzyloxy)phenylamino]-quinazolin-6-yl}-acrylamide p-Toluenesulfonate.

The said protic solvent is water or the mixture of water and an alcohol, such as methanol or ethanol, and particularly preferred is water. The said aprotic solvent is selected from the group consisting of tetrahydrofuran, ether, dichloromethane, acetone, acetonitrile, DMF, and the mixtures thereof, preferably tetrahydrofuran.

The volume ratio of the protic solvent to the aprotic solvent in the mixture of a protic solvent and an aprotic solvent is 1:2~4, preferably 1:3~4.

The solution of Form A in the above step (a) has a concentration of 2~10 g/100 mL, preferably 4-8 g/100 mL.

Usually, the cooling as mentioned above shall be carried out till the temperature is under room temperature. The standing time as mentioned above is most preferred when Form B is completely precipitated, and the better standing time can be readily determined by one skilled in the art through several experiments.

Also, the present invention provides a process for preparing Form C, comprising the steps of:

(a) dissolving the above crystalline form A of the N-{4-[3-chloro-4-(3-fluoro-benzyloxy)phenylamino]-quinazolin-6-yl}-acrylamide p-Toluenesulfonate in the mixture of a protic solvent and an aprotic solvent to form a solution;

(b) adding dropwise a solution formed from p-Toluenesulfonic acid in said mixture of a protic solvent and an aprotic solvent under stirring and controlling the molar ratio of Form A to p-Toluenesulfonic acid in the range of 1:1~6, preferably 1:3~6; and (c) resulting in a crystalline precipitate, letting the resulting mixture stand, and filtering out and washing the crystal to obtain the target crystal.

The said protic solvent is water or the mixture of water and an alcohol, such as methanol or ethanol, and especially preferred is water. The aprotic solvent is selected from the group consisting of tetrahydrofuran, ether, dichloromethane, acetone, acetonitrile, DMF, and the mixtures thereof, preferably tetrahydrofuran.

The volume ratio of the protic solvent to the aprotic solvent in the mixture of a protic solvent and an aprotic solvent is 1:1~5, preferably 1:3~4.

The solution of Form A in the above step (a) has a concentration of 3~7 g/100 mL, preferably 4~6 g/100 mL.

The solution of p-Toluenesulfonic acid in the above step (b) has a concentration of 10~30 g/100 mL, preferably 15~25 g/100 mL.

In the present invention, the term "protic solvent" refers to a type of solvent with hydroxyl (i.e., —OH), such as water, an alcohol, such as methanol, ethanol, and so on, preferably water or the mixture of water and an alcohol, such as methanol or ethanol, especially preferably water. The term "aprotic solvent" refers to an organic solvent without hydroxyl, such as tetrahydrofuran, ether, dichloromethane, acetone, acetonitrile, DMF, and the mixtures thereof, preferably tetrahydrofuran.

In accordance with the third aspect of the present invention, there is provided pharmaceutical compositions comprising the crystal/polymorphic form according to the present invention and a pharmaceutically acceptable carrier. In addition, the present invention also provides a method for the treatment and/or prevention of tumors in a mammal, comprising administering the crystal/polymorphic form of the present invention to a mammal which needs such treatment or prevention in an amount effective in treatment and/or prevention.

Said pharmaceutical composition may be administered to a mammal (e.g., human) by oral, rectal, parenteral (e.g., intravenous, intramuscular or subcutaneous), or topical route. When the pharmaceutical composition is used, the pharmaceutical composition comprising the crystal/polymorphic form of the present invention in an amount effective in treatment or prevention is administered to a mammal (e.g., human) which needs such treatment or prevention. The term "an amount effective in treatment or prevention" refers to an amount of the active compound sufficient to cause the biological or medical response in a mammal (e.g., human) sought by the veterinarian or clinical physician. Ordinary physician, veterinarian and clinical physician can easily determine the effective amount of the crystal/polymorphic form of the present invention for the treatment or prevention of the indicated diseases, which is usually 0.01~20 mg/kg of a patient's body weight per day, preferably 0.1~10 mg/kg of a patient's body weight per day. More specifically, the daily dosage for a person of a body weight of 60 kg is usually 1~1000 mg, preferably 20~500 mg. It is certain that the specific dosage will depend upon a number of factors such as administration route, age, gender, weight and health conditions of a patient, as well as the special conditions to be treated, all of which are well within the abilities of a skilled physician. The term "mammal" used herein includes, but is not limited to, cat, dog, rabbit, goat, sheep, mouse, rat, human and the like, and human is particularly preferred.

The pharmaceutical composition provided in the present invention may further comprise one or more other agents for the treatment and/or prevention of tumors. Said other agents for the treatment and/or prevention of tumors may be selected from the drugs which act on the chemical structure of DNA, such as Cisplatin and the like, the drugs having influence on the synthesis of nucleic acid such as Methotrexate (MTX), 5-Fluorouracil (5FU) and the like, the drugs which affect the transcription of nucleic acid such as Adriamycin, Epirubicin, Aclacinomycin, Mitramycin and the like, the drugs which act on the synthesis of tubulin such as paclitaxel, Vinorelbine and the like, aromatized enzyme inhibitors such as Aminoglutethimide, Lentaron, Letrozole, and Anastrozole and the like, and inhibitors of the cell signal pathway such as Imatinib, Gefitinib, Erlotinib, and the like.

Both the crystal/polymorphic form and the pharmaceutical composition of the present invention can be formulated in solid dosage forms for oral administration, including capsules, tablets, pills, powders, granules, dragees and the like. In such solid dosage forms, the crystal/polymorphic form provided in the present invention can be mixed with at least one conventional inert excipient (or carrier). The inert excipient (or carrier) includes but is not limited to (a) fillers or solubilizers, such as starch, lactose, sucrose, glucose, mannitol and silicic acid; (b) binders, such as hydroxymethyl cellulose, alginate, gelatin, polyvinylpyrrolidone, sucrose and arabic gum; (c) humectants, such as glycerol; (d) disintegrants, such as agar, calcium carbonate, potato starch or cassava starch, alginic acid, some composite silicates, polyvinylpolypyrrolidone and sodium carbonate; (e) retarding solvents, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol, sodium dodecyl sulfate, or the mixtures thereof. Capsules, tablets and pills can also contain buffers.

The solid dosage forms such as tablets, dragees, capsules, pills and granulas can be prepared with coating and shell materials, such as enteric coatings or other materials well known in the art. They may contain an opacifier. Besides, the release of the active compound in the composition can be carried out at a certain part of the alimentary canal in a delayed manner. When necessary, the active compound can be formulated in microencapsulated form with one or more of the above excipients.

The crystal/polymorphic form and the pharmaceutical composition of the present invention can also be formulated in a liquid dosage form for oral administration, including pharmaceutically acceptable emulsion, solution, suspension, syrup or tincture. In addition to the crystalline form provided in the present invention as an active compound, the liquid dosage form may also contain inert diluents commonly used in the art, such as water or other solvents, solubilizers and emulsifiers, such as ethanol, isopropanol, ethyl carbonate, ethyl acetate, propanediol, 1,3-butanediol, dimethylformamide and plant oils, in particular, cottonseed oil, peanut oil, corn germ oil, olive oil, castor oil and sesame oil, or the mixtures thereof. Apart from these inert diluents, the composition can also comprise auxiliaries, such as wetting agents, emulsifying and suspending agents, sweeteners, flavoring agents and perfuming agents.

When the pharmaceutical composition of the present invention is present as a suspension, the suspension may further comprise, in addition to the crystal/polymorph provided in the present invention, suspending agents, such as ethoxylated isooctadecanol, polyoxyethylene sorbitol and dehydrated sorbitan ester, microcrystalline cellulose, aluminium methoxide and agar, or the mixtures thereof, and the like.

The crystal/polymorphic form and the pharmaceutical composition of the present invention can also be formulated into a dosage form for parenteral injection, including physiologically acceptable sterile aqueous or nonaqueous solution, dispersion, suspension or emulsion, and sterile powder which can be redissolved into sterile injectable solution or dispersion. Aqueous and nonaqueous carriers, diluents, solvents or excipients can be used to prepare said sterile aqueous or nonaqueous solution, dispersion, suspension or emulsion. Suitable aqueous and nonaqueous carriers, diluents, solvents or excipients include water, ethanol, a polyol and suitable mixtures thereof.

The crystal/polymorphic form and the pharmaceutical composition of the present invention can be formulated into a dosage form for topical administration, including ointment, powder, patch, spray and inhalant. The crystal/polymorphic form provided in the present invention can be mixed with physiologically acceptable carriers and any preservatives, buffers, or required propellants, if necessary, under sterile condition.

In another aspect, the crystal/polymorphic form provided in the present invention can be used in the preparation of medicaments for the treatment and/or prevention of the diseases mediated by protein tyrosine kinases. Said diseases include tumors, especially malignant tumors, such as breast cancer, non-small cell lung cancer, ovarian cancer, gastric cancer, colonic cancer, pancreatic cancer, epidermoid squamous cancer and the like.

The crystal/polymorphic form of the present invention may be administered alone or in combination with other pharmaceutically acceptable therapeutic agents, especially with other anti-tumor drugs. The therapeutic agents include, but are not limited to, the drugs which act on the chemical structure of DNA, such as Cisplatin and the like, the drugs which affect the synthesis of nucleic acid such as Methotrexate (MTX), 5-Fluorouracil (5FU) and the like, the drugs which affect the transcription of nucleic acid such as Adriamycin, Epirubicin, Aclacinomycin, Mitramycin and the like, the drugs which act on synthesis of tubulin such as Paclitaxel, Vinorelbine and the like, aromatized enzyme inhibitors such as Aminoglutethimide, Lentaron, Letrozole, Anastrozole and the like, inhibitors of the cell signal pathway such as Imatinib, Gefitinib, Erlotinib, and the like. The various ingredients to be combined can be administered simultaneously or sequentially, and can be administered either in a single formulation or in separate formulations. Such a combination includes not only the combination of the crystal/polymorphic form provided in the present invention with one additional active agent but also the combination of the crystal/polymorphic form of the present invention with two or more other active agents.

The main advantages of the polymorphic forms of the present invention include:

(a) The polymorphs of N-{4-[3-chloro-4-(3-fluoro-benzyloxy)phenylamino]-quinazolin-6-yl}-acrylamide p-Toluenesulfonate salt provided in the present invention are not apt to absorb moisture, and have the relatively good thermal stability and light stability;

(b) It is proved by experiments in vivo that the polymorphs provided in the present invention possess excellent bioavailability in animals;

(c) It is proved by experiments that the polymorphs provided in the present invention possess the excellent anti-tumor activity;

(d) It is proved by experiments in vivo that the polymorphs provided in the present invention possess low toxicity and high safety of administration in animals.

From the above description of the method for the preparation of polymorphs, the polymorphs of the p-Toluenesulfonate of the compound of formula (I) are obtained in the present invention by use of the different solubility of the p-Toluenesulfonate of the compound of formula (I) in different solvents, which achieves the goal of purifying the p-Toluenesulfonate of the compound of formula (I). This purification method is easy to operate, and is suitable for industrial production in a large scale.

Figure 1:
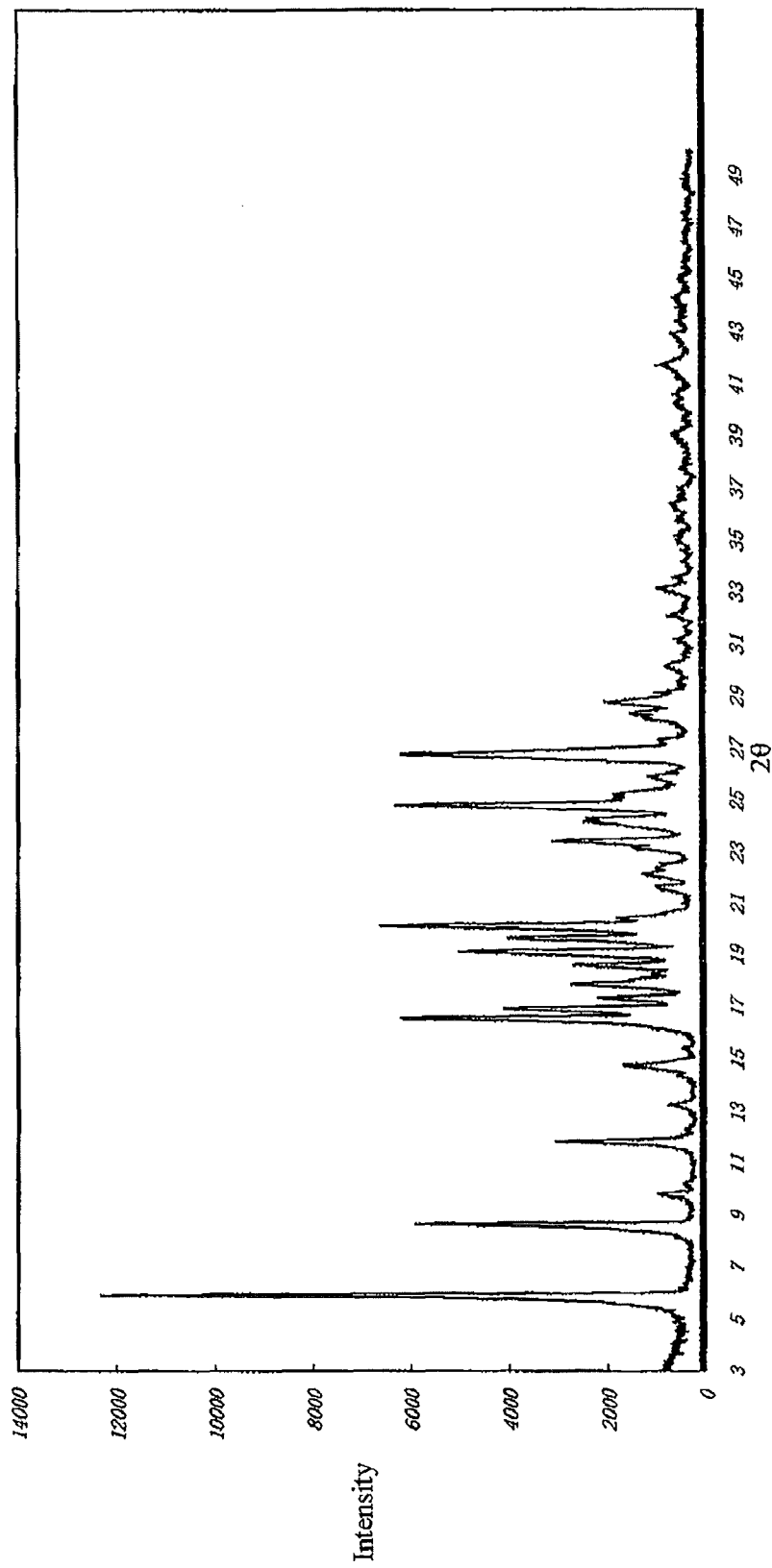
FIG. 1 shows the X-ray powder diffraction pattern of Form A of the N-{4-[3-chloro-4-(3-fluoro-benzyloxy)phenylamino]-quinazolin-6-yl}-acrylamide p-Toluenesulfonate.

The present invention will now be further described by certain examples. These examples are only to illustrate the present invention, but are not intended to limit its protection scope. For the experimental methods in the following examples for which the specific conditions are not indicated, the conventional conditions or the conditions suggested by the manufacturers are followed. The materials as used are obtained commercially or may be easily obtained by the person skilled in the art according to the methods in known literatures. As used herein, the abbreviation THF represents tetrahydrofuran; DMSO represents dimethyl sulfoxide; DMF represents dimethylformamide; PVPP represents polyvinylpolypyrrolidone; PVP represents polyvinylpyrrolidone; ig refers to intragastric administration, and iv refers to intravenous injection. Unless otherwise indicated, the amounts and percents are measured by weight.

EXAMPLES

Example 1

Preparation of N-{4-[3-chloro-4-(3-fluoro-benzyloxy)phenylamino]-quinazolin-6-yl}-acrylamide Step A: Preparation of 4-[3-chloro-4-(3-fluoro-benzyloxy)phenylamino]-6-nitro-quinazoline 1.20 g (5.7 mmol) of 4-chloro-6-nitro-quinazoline (prepared by referring to WO 2007/082434) and 1.37 g (5.6 mmol) of 4-(3-fluoro-benzyloxy)-3-chloro-aniline (prepared by referring to WO 2007/082434) were dissolved in 80 mL of isopropanol and refluxed for 3 hours. A large amount of yellow solid was precipitated from the system, and was filtered. The filter cake was washed with a saturated sodium bicarbonate solution till pH=8 and dried under vacuum to obtain 1.62 g (3.75 mmol) of yellow solid, which was identified as the compound 4-[3-chloro-4-(3-fluoro-benzyloxy)phenylamino]-6-nitro-quinazoline with a yield of 67%.

$^1$H-NMR(400 MHz, CDCl$_3$): δ11.30(1H, br), 9.54-9.48 (1H, m), 8.45-8.41(1H, m), 8.31-8.25(1H, m), 7.98-7.89(1H, m), 7.50-7.47(1H, m), 7.35-7.26 (1H, m), 7.05-6.96(1H, m), 6.90-6.80(2H, m), 7.74-7.60(2H, m), 4.84(2H, s).

Step B: Preparation of 4-[3-chloro-4-(3-fluoro-benzyloxy)phenylamino]-6-amino-quinazoline 1.60 g (3.77 mmol) of compound 4-[3-chloro-4-(3-fluoro-benzyloxy)phenylamino]-6-nitro-quinazoline prepared according to the method of Step A, 1.05 g (18.85 mmol, 5 eq) of reduced Fe powders, 2 mL of glacial acetic acid and 40 mL of methanol were added to a flask equipped with a refluxing condenser and refluxed for 2.5 hours in a 85° C. oil-bath. The Fe powders were removed by filtration. The filtrate was diluted with ethyl acetate and washed sequentially with sodium bicarbonate solution and water. The organic phase was dried and concentrated to obtain 900 mg (2.28 mmol) of a yellow solid, which compound was identified as 4-[3-chloro-4-(3-fluoro-benzyloxy)phenylamino]-6-amino-quinazoline with a yield of 61%.

$^1$H-NMR(400 MHz, DMSO): δ9.32(1H, s), 8.31(1H, s), 8.04(1H, d, J=2.64 Hz), 7.73(1H, dd, J=2.64 Hz, 8.80 Hz), 7.54-7.43(2H, m), 7.36-7.28(3H, m), 7.26-7.14(3H, m), 5.57 (2H, br), 5.27(2H, s).

Step C: Preparation of N-{4-[3-chloro-4-(3-fluoro-benzyloxy)phenylamino]-quinazolin-6-yl}-acrylamide 1.2 g (3.04 mmol) of 4-[3-chloro-4-(3-fluoro-benzyloxy)phenylamino]-6-amino-quinazoline prepared according to the method of Step B, 0.6 mL (4.58 mmol, 1.5 eq) of triethylamine, 0.28 mL (3.33 mmol, 1.1 eq) of acryloyl chloride and 40 mL of THF were added under the cooling by an ice-bath. The reaction temperature rose to room temperature slowly. The reaction was stopped after 3 hours. The resultant mixture were filtered, and the filter cake was washed with water to neutral and dried to obtain 1.0 g (2.23 mmol) of a yellow solid, which compound was identified as N-{4-[3-chloro-4-(3-fluoro-benzyloxy)phenylamino]-quinazolin-6-yl}-acrylamide with a yield of 67%. MS: 449, mp: 222-225° C.

$^1$H-NMR(400 MHz, CDCl$_3$+DMSO): δ8.75(1H, s), 8.60-8.52(2H, m), 7.81(1H, d, J=2.44 Hz), 7.69(2H, s), 7.54(1H, dd, J=2.56 Hz, 8.92 Hz), 7.30-7.22(2H, m), 7.18-7.08(2H, m), 6.96-6.86(2H, m), 6.37(2H, d, J=5.86 Hz), 5.67(1H, t, J=5.86 Hz), 5.06 (2H, s).

Example 2

Preparation of the Crystal of p-Toluenesulfonate of N-{4-[3-chloro-4-(3-fluoro-benzyloxy)phenylamino] quinazolin-6-yl}-acrylamide 3 g (6.68 mmol) of the compound N-{4-[3-chloro-4-(3-fluoro-benzyloxy)phenylamino]-quinazolin-6-yl}-acrylamide prepared according to the method of Example 1 was dissolved in the mixture of tetrahydrofuran and methanol (THF/CH$_3$OH=2/1, 30 mL), and 24 mL of a solution of p-toluenesulfonic acid (1 eq, 1.27 g) in the mixture of tetrahydrofuran and methanol (THF/CH$_3$OH=1/1) was added dropwise into the system slowly, and then a large amount of yellow solid was slowly precipitated from the system after the addition was finished. The solid was filtered, and washed with water and dried under vacuum to obtain 2.6 g (4.19 mmol) of yellow crystalline powder with a yield of 63% and a purity of 92.5%.

Example 3

Figure 5:
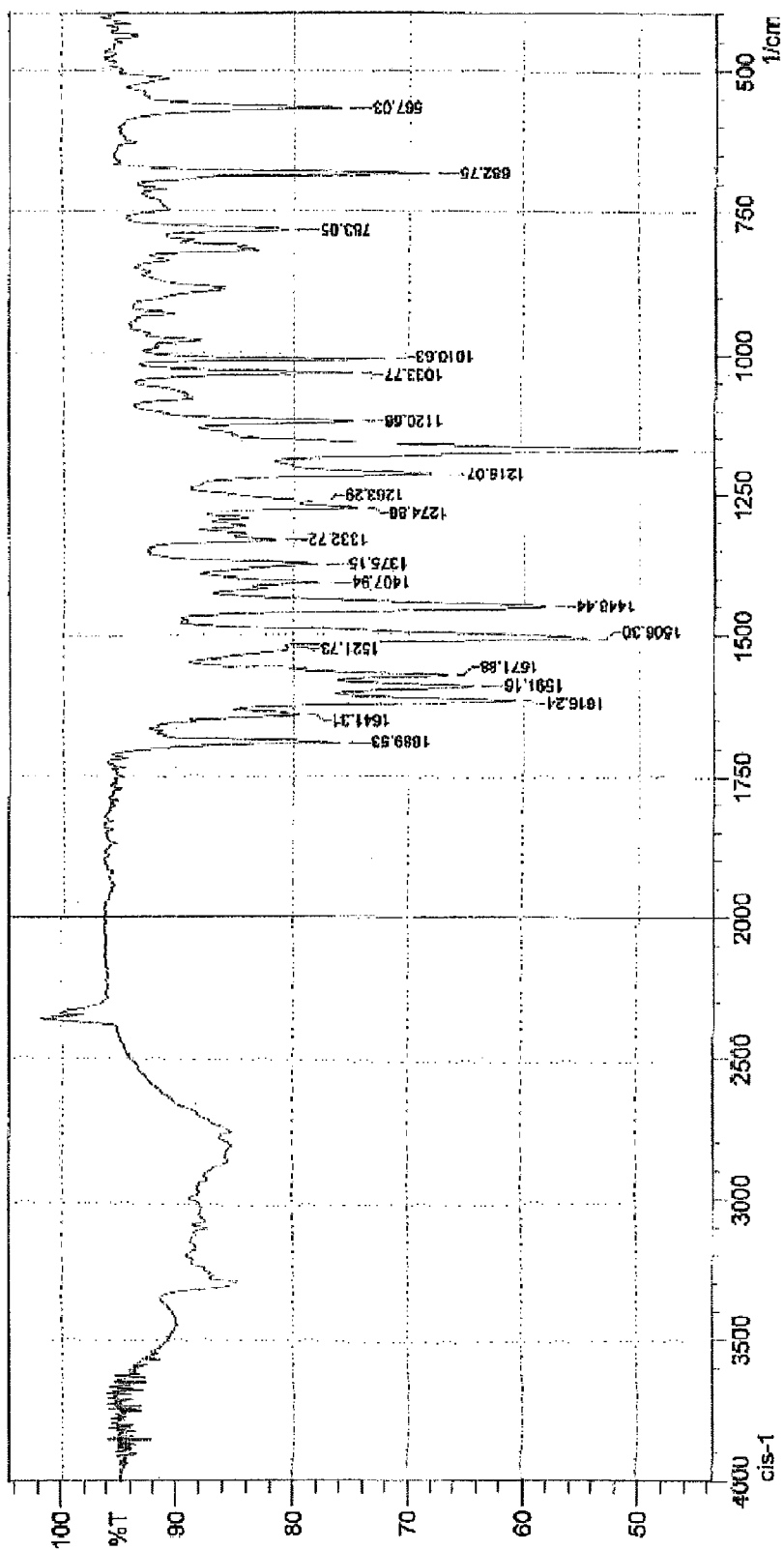
FIG. 5 shows IR spectrum of Form A of the N-{4-[3-chloro-4-(3-fluoro-benzyloxy)phenylamino]-quinazolin-6-yl}-acrylamide p-Toluenesulfonate.

Preparation of Form A of p-Toluenesulfonate of N-{4-[3-chloro-4-(3-fluoro-benzyloxy)phenylamino] quinazolin-6-yl}-acrylamide 3 g (6.68 mmol) of the compound N-{4-[3-chloro-4-(3-fluoro-benzyloxy)phenylamino]-quinazolin-6-yl}-acrylamide prepared according to the method of Example 1 was dissolved in the mixture of tetrahydrofuran and methanol (THF/CH$_3$OH=1/1, 50 mL), and a 38 mL solution of p-toluenesulfonic acid (6 eq, 7.62 g) in the mixture of tetrahydrofuran and methanol (THF/CH$_3$OH=1/1) was added dropwise into the system slowly, and then a large amount of green yellow solid was slowly precipitated from the system during the addition. The solid was filtered, and the filter cake was washed with water and dried under vacuum to obtain 2.93 g of green yellow crystalline powder with a yield of 70%. The X-ray powder diffraction pattern of the obtained crystal was shown in FIG. 1. The IR spectrum of the crystal was shown in FIG. 5. The melting point of the crystal was 245° C. This crystalline form was defined as Form A in the present application.

Example 4

Preparation of Form A of p-Toluenesulfonate of N-{4-[3-chloro-4-(3-fluoro-benzyloxy)phenylamino] quinazolin-6-yl}-acrylamide 3 g (6.68 mmol) of the compound N-{4-[3-chloro-4-(3-fluoro-benzyloxy)phenylamino]-quinazolin-6-yl}-acrylamide prepared according to the method of Example 1 was dissolved in the mixture of tetrahydrofuran and methanol (THF/CH$_3$OH=1/3, 60 mL), and a 38 mL solution of p-toluenesulfonic acid (6 eq, 7.62 g) in the mixture of tetrahydrofuran and methanol (THF/CH$_3$OH=1/1) was added dropwise into the system slowly, and then a large amount of green yellow solid was slowly precipitated from the system during the addition. The solid was filtered, and the filter cake was washed with water and dried under vacuum to obtain 2.52 g of green yellow crystalline powder with a yield of 61%. The X-ray powder diffraction pattern of the obtained crystal was shown in FIG. 1. The IR spectrum of the crystal was shown in FIG. 5. The melting point of the crystal was 245° C. This crystalline form was defined as Form A in the present application.

Example 5

Figure 2:
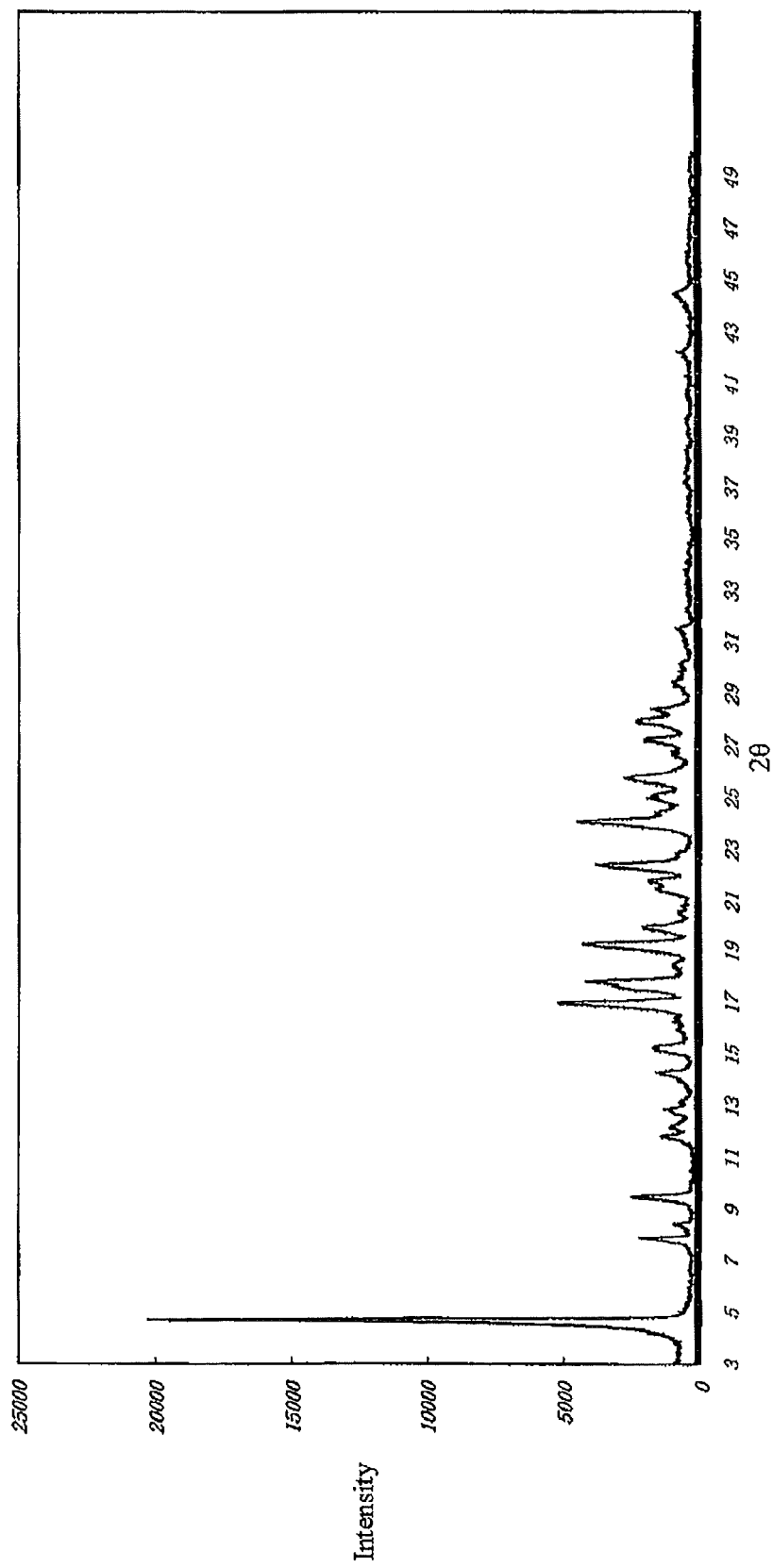
FIG. 2 shows the X-ray powder diffraction pattern of Form B of the N-{4-[3-chloro-4-(3-fluoro-benzyloxy)phenylamino]-quinazolin-6-yl}-acrylamide p-Toluenesulfonate.
Figure 6:
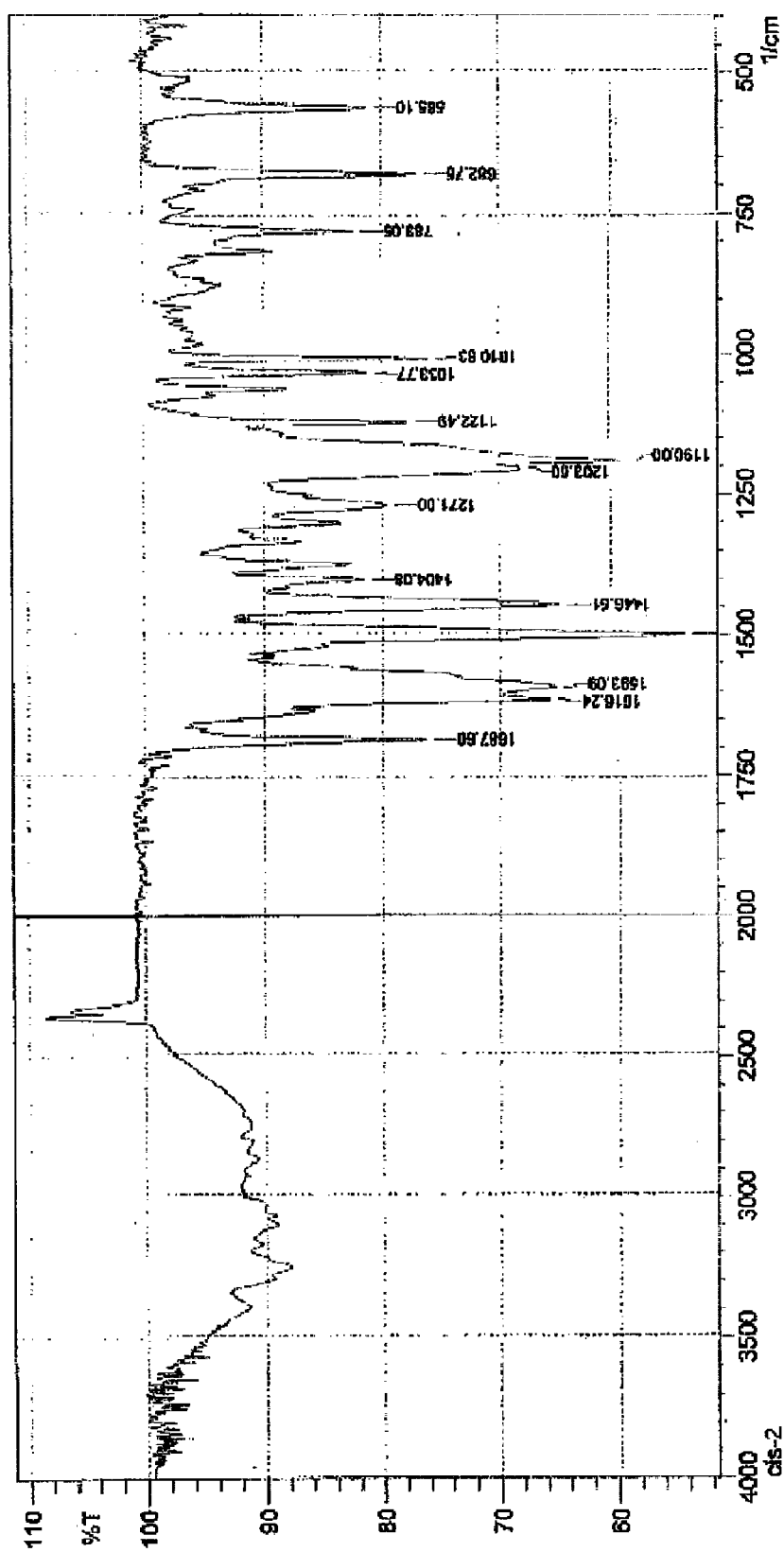
FIG. 6 shows IR spectrum of Form B of the N-{4-[3-chloro-4-(3-fluoro-benzyloxy)phenylamino]-quinazolin-6-yl}-acrylamide p-Toluenesulfonate.

Preparation of Form B of p-Toluenesulfonate of N-{4-[3-chloro-4-(3-fluoro-benzyloxy)phenylamino]quinazolin-6-yl}-acrylamide 3 g (4.84 mmol) of Form A of p-Toluenesulfonate of N-{4-[3-chloro-4-(3-fluoro-benzyloxy)phenylamino]-quinazolin-6-yl}-acrylamide prepared according to the method of Example 3 or 4 was added to the mixture of tetrahydrofuran and water (THF/H$_2$O=4/1, 70 mL), and the resultant mixture was slowly risen to a temperature of 65° C. which was continuously kept for 20 min and then cooled to the room temperature slowly, and then stood at 2° C. for 16 h. The resultant mixture were filtered, and the filter cake was washed with water and dried under vacuum to obtain 1.68 g pale yellow crystalline powder with a yield of 56%. The X-ray powder diffraction pattern of the obtained crystal was shown in FIG. 2. The IR spectrum of the crystal was shown in FIG. 6. The melting point of the crystal was 235.4° C. This crystalline form was defined as Form B in the present application.

Example 6

Preparation of Form B of p-Toluenesulfonate of N-{4-[3-chloro-4-(3-fluoro-benzyloxy)phenylamino]quinazolin-6-yl}-acrylamide 3 g (4.84 mmol) of Form A of p-Toluenesulfonate of N-{4-[3-chloro-4-(3-fluoro-benzyloxy)phenylamino]-quinazolin-6-yl}-acrylamide prepared according to the method of Example 3 or 4 was added in the mixture of tetrahydrofuran and water (THF/H$_2$O=2/1, 70 mL), and the resultant mixture was slowly risen to a temperature of 65° C. which was continuously kept for 20 min and then cooled to the room temperature slowly, and then stood at 2° C. for 16 h. The resultant mixture were filtered, and the filter cake was washed with water and dried under vacuum to obtain 2.30 g pale yellow crystalline powder with a yield of 76%. The X-ray powder diffraction pattern of the obtained crystal was shown in FIG. 2. The IR spectrum of the crystal was shown in FIG. 6. The melting point of the crystal was 235.4° C. This crystalline form was defined as Form B in the present application.

Example 7

Figure 3:
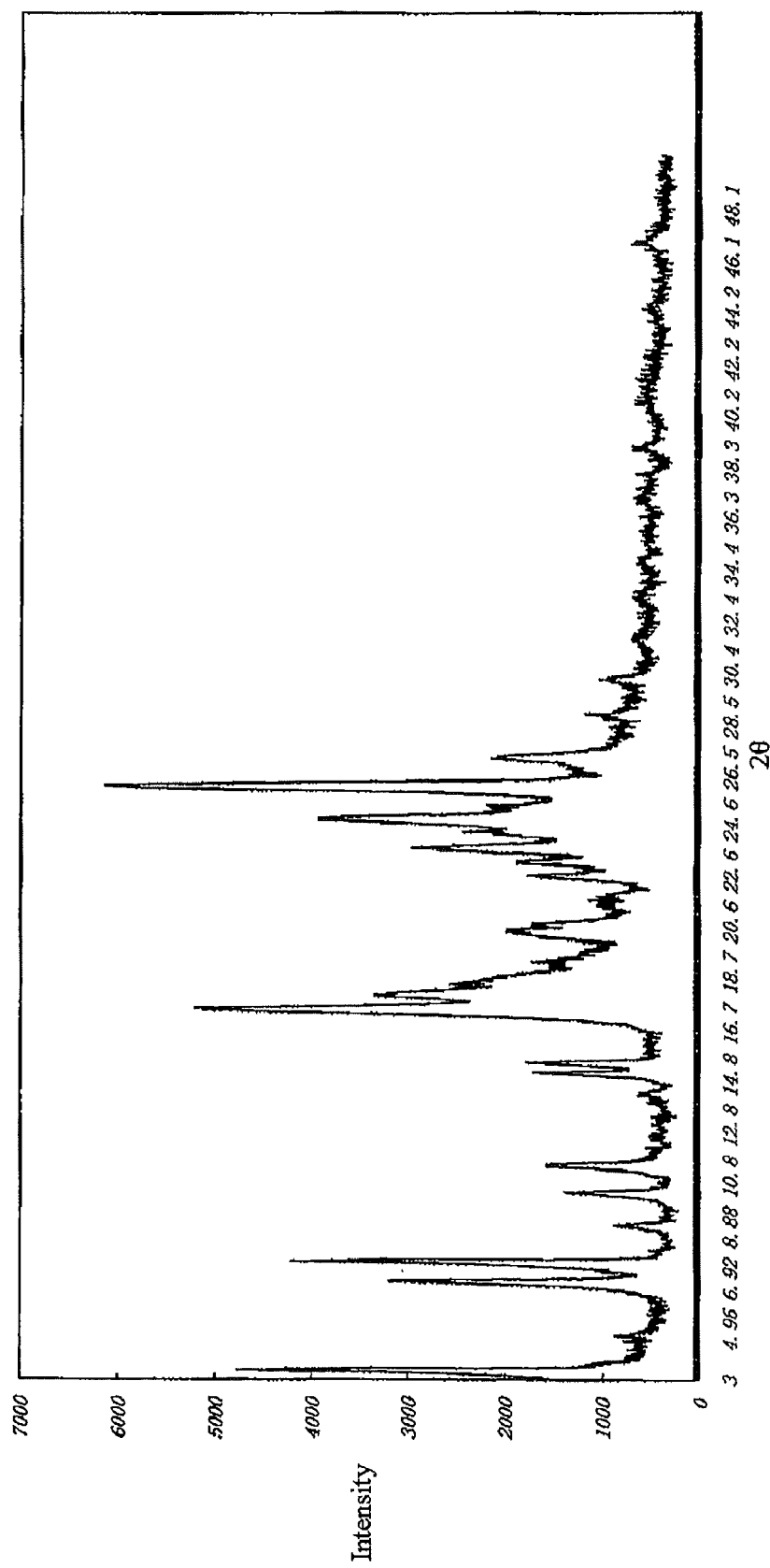
FIG. 3 shows the X-ray powder diffraction pattern of Form C of the N-{4-[3-chloro-4-(3-fluoro-benzyloxy)phenylamino]-quinazolin-6-yl}-acrylamide p-Toluenesulfonate.
Figure 4:
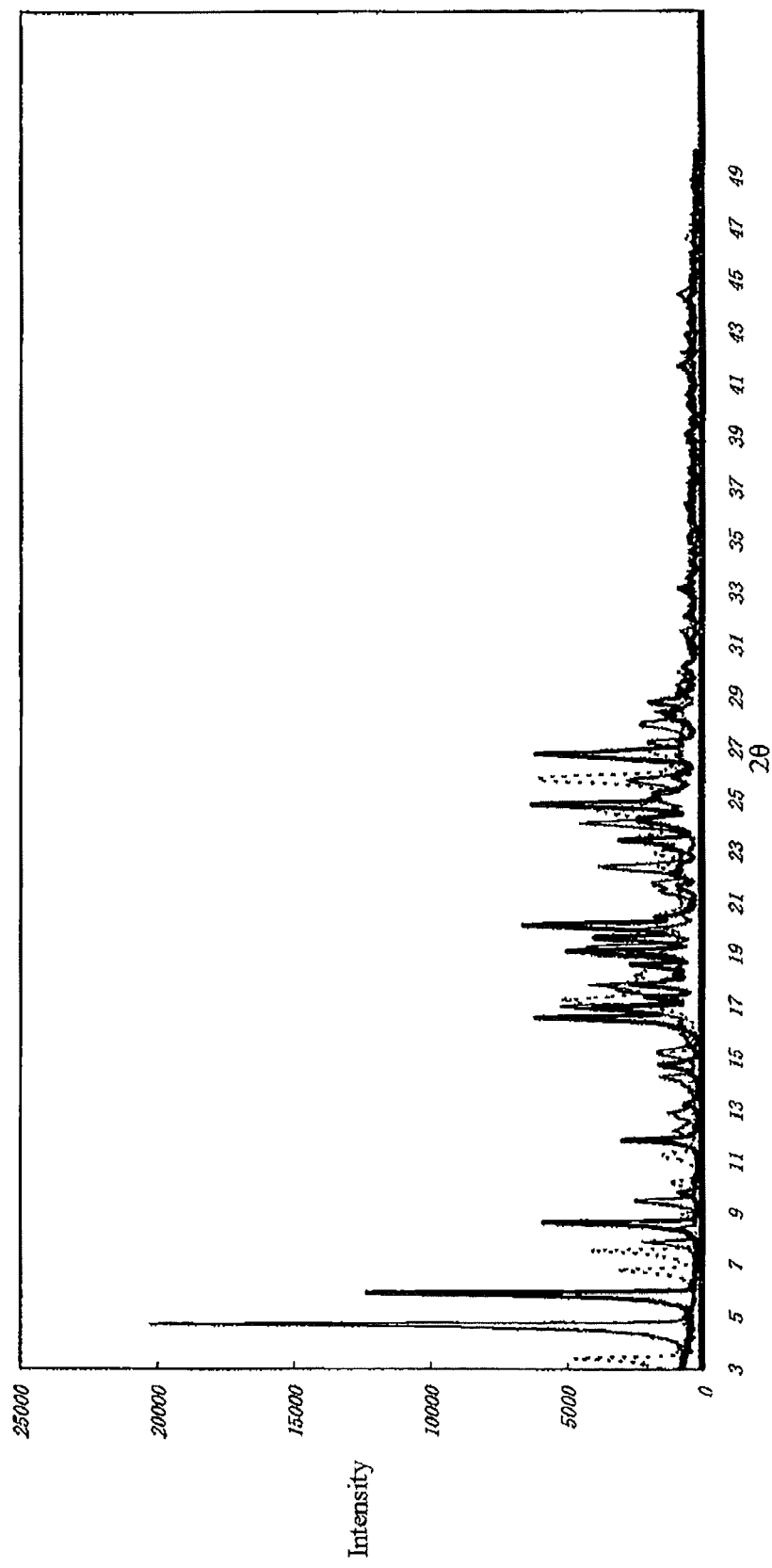
FIG. 4 shows the superposed pattern of the X-ray powder diffraction patterns of Forms A, B and C of the N-{4-[3-chloro-4-(3-fluoro-benzyloxy)phenylamino]-quinazolin-6-yl}-acrylamide p-Toluenesulfonate, wherein the diffraction peaks of Form A are represented by thick real lines, Form B by fine real lines, and Form C by dashed lines.
Figure 7:
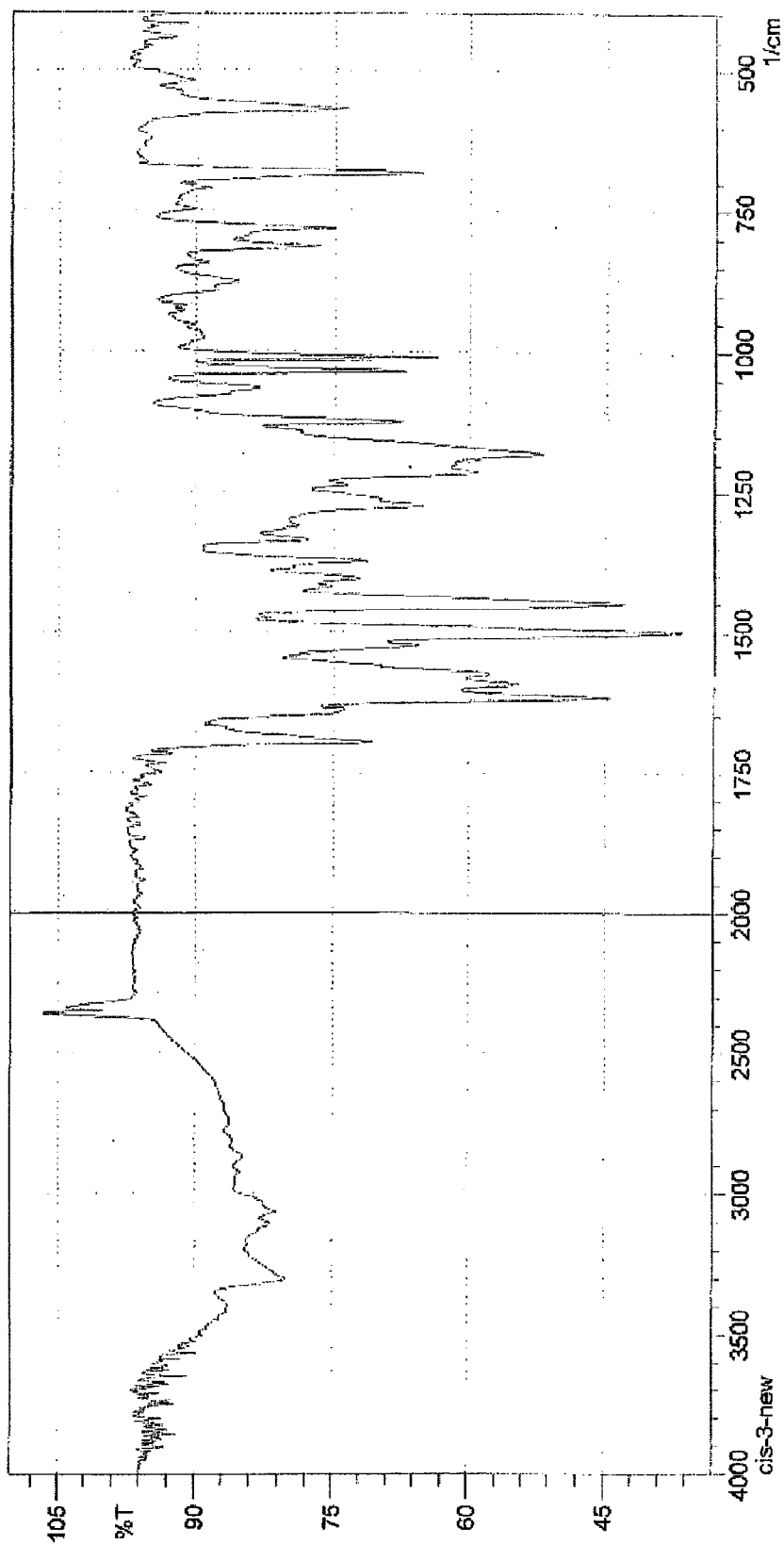
FIG. 7 shows IR spectrum of Form C of the N-{4-[3-chloro-4-(3-fluoro-benzyloxy)phenylamino]-quinazolin-6-yl}acrylamide p-Toluenesulfonate.

Preparation of Form C of p-Toluenesulfonate of N-{4-[3-chloro-4-(3-fluoro-benzyloxy)phenylamino]quinazolin-6-yl}-acrylamide 3 g (4.84 mmol) of Form A of p-Toluenesulfonate of N-{4-[3-chloro-4-(3-fluoro-benzyloxy)phenylamino]-quinazolin-6-yl}-acrylamide prepared according to the method of Example 3 or 4 was added in the mixture of tetrahydrofuran and water (THF/H$_2$O=3/1, 60 mL), and a 38 mL solution of p-toluenesulfonic acid (6 eq, 7.62 g) in the mixture of tetrahydrofuran and methanol (THF/CH$_3$OH=2/1) was added dropwise into the system slowly, and then a large amount of yellow solid was slowly precipitated from the system during the addition. The solid was filtered, and the filter cake was washed with water and dried under vacuum to obtain 2.85 g of yellow crystalline powder with a yield of 95%. The X-ray powder diffraction pattern of the obtained crystal was shown in FIG. 3. The IR spectrum of the crystal was shown in FIG. 7. The melting point of the crystal was 244° C. This crystalline form was defined as Form C in the present application.

Example 8

Preparation Form C of p-Toluenesulfonate of N-{4-[3-chloro-4-(3-fluoro-benzyloxy)phenylamino]quinazolin-6-yl}-acrylamide 3 g (4.84 mmol) of Form A of p-Toluenesulfonate of N-{4-[3-chloro-4-(3-fluoro-benzyloxy)phenylamino]-quinazolin-6-yl}-acrylamide prepared according to the method of Example 3 or 4 was added in the mixture of tetrahydrofuran and water (THF/H$_2$O=4/1, 60 mL), and a 38 mL solution of p-toluenesulfonic acid (6 eq, 7.62 g) in the mixture of tetrahydrofuran and methanol (THF/CH$_3$OH=2/1) was added dropwise into the system slowly, and then a large amount of yellow solid was slowly precipitated from the system during the addition. The solid was filtered, and the filter cake was washed with water and dried under vacuum to obtain 1.95 g of yellow crystalline powder with a yield of 65%. The X-ray powder diffraction pattern of the obtained crystal was shown in FIG. 3. The IR spectrum of the crystal was shown in FIG. 7. The melting point of the crystal was 244° C. This crystalline form was defined as Form C in the present application.

Example 9

Thermal Stability Test

A small amount of Form A was taken to be placed under a high temperature environment of 60° C. to be stored for a month. The purity of Form A was detected at 0, and 30 days, which was based to deduce the thermal stability of Form A. The thermal stability of Form B and Form C were also deduced by this method. The results of the test were shown in the following table.

| | Form | | | | | | | | |
|---|---|---|---|---|---|---|---|---|---|
| | Form A | | | Form B | | | Form C | | |
| | Detect time (day) | | | | | | | | |
| | 0 | 10 | 30 | 0 | 10 | 30 | 0 | 10 | 30 |
| Purity (%) | 98.64 | 98.64 | 98.64 | 99.26 | 99.21 | 99.11 | 99.03 | 97.08 | 97.55 |

The above results of the test indicate that stored under the high temperature of 60° C., Form A and Form B almost do not change as to the purity, but the purity of Form C slightly decreases. It is indicated that Form A and Form B provided in the present invention have the excellent thermal stability, and Form C has the good thermal stability.

Example 10

Light Stability Test

A small amount of Form A was taken to be placed under the environment of illumination with an intensity of 4500 lx±500 lx to be stored for a month. The purity of Form A was detected at 0, 10 and 30 days, which was based to deduce to the light stability of Form A. The light stability of Form B and Form C were also deduced by this method. The results of the test were shown in the following table.

| | | | | Form | | | | | |
|---|---|---|---|---|---|---|---|---|---|
| | Form A | | | Form B | | | Form C | | |
| | | | | Detect time | | | | | |
| | 0 | 10 | 30 | 0 | 10 | 30 | 0 | 10 | 30 |
| Purity (%) | 98.64 | 98.16 | 97.24 | 99.26 | 99.26 | 99.24 | 99.03 | 98.54 | 98.42 |

The above results of the test indicate that stored under the environment of illumination with an intensity of 4500 lx±500 lx, Form B almost does not change as to purity, but the purities of Form A and Form C slightly decrease. It is indicated that Form B provided in the present invention has the excellent light stability, and Form A and Form C have the good light stability.

Example 11

Hygroscopicity Test

A small amount of Form A was taken to be placed under a high moisture environment of 92.5% to be stored for a month. The purity of Form A was detected at 0, 10 and 30 days, which was based to deduce the hygroscopicity of Form A. The hygroscopicities of Form B and Form C were also deduced by this method. The results of the test were shown in the following table.

| | | | | Form | | | | | |
|---|---|---|---|---|---|---|---|---|---|
| | Form A | | | Form B | | | Form C | | |
| | | | | Detect time | | | | | |
| | 0 | 10 | 30 | 0 | 10 | 30 | 0 | 10 | 30 |
| Purity (%) | 98.64 | 98.62 | 98.62 | 99.26 | 99.25 | 99.24 | 99.03 | 98.27 | 98.08 |

The above results of the test indicate that stored under a high moisture environment of 92.5%, Form A and Form B almost do not change as to purity, but the purity of Form C slightly decreases. It is indicated that the Form A and Form B provided in the present invention are very stable under the environment of high moisture, and Form C is comparatively stable under the environment of high moisture.

The results of the Examples 9-11 indicate that the polymorphs provided in the present invention are relatively stable under the environment of high temperature, illumination or high moisture.

Example 12

Test on the Drug Absorption in SD Rat (Sprague Dawley Rat)

Intragastric administration (ig): 16 healthy SD rats, male, weighed 200~250 g, and grouped into 4 groups randomly, were each administered intragastrically with a drug: the compound (21.68 mg/kg) prepared according to Example 1, Form A, B or C of p-toluenesulfonate of the compound (30 mg/kg). The blood samples were collected at 0.5, 1.0, 1.5, 2.0, 3.0, 5.0, 7.0, 9.0, 12 and 24 hours after administration, which were then isolated to prepare the plasma. The concentration of the drug in the plasma was determined by means of liquid chromatography/mass spectrometry, and the concentration-time curve was obtained.

The main pharmacokinetics parameters were shown in the following table:

| Compound | Dosage (mg/kg) | $T_{max}$ (h) | $C_{max}$ (ng/mL) | $AUC_{0-t}$ (ng·h/mL) | $T_{1/2}$ (h) |
|---|---|---|---|---|---|
| Compound of formula (I) | 21.68 | 0.75 | 32 | 106 | 1.81 |
| Form A | 30 | 2.83 | 187 | 977 | 1.49 |
| Form B | 30 | 1.25 | 253 | 978 | 1.23 |
| Form C | 30 | 2.25 | 161 | 577 | 1.27 |

Intravenous injection (iv): 4 healthy SD rats, male and weighed 200~250 g, were intravenously administered with p-toluenesulfonate of the compound of formula (I) (5 mg/kg). The blood samples were collected at 5 min, 15 min, 0.5, 1.5, 2.0, 3.0, 4.0, 5.0 and 7.0 hours after administration, which were then isolated to prepare the plasma. The concentration of the compound in the plasma was determined by means of liquid chromatography/mass spectrometry, and the concentration-time curve was obtained.

The main pharmacokinetics parameters were shown in the following table:

| Compound | Dosage (mg/kg) | $T_{max}$ (h) | $C_{max}$ (ng/mL) | $AUC_{0-t}$ (ng·h/mL) | $T_{1/2}$ (h) |
|---|---|---|---|---|---|
| p-Toluenesulfonate | 5 | 0.083 | 1745 | 1860 | 1.55 |

Corrected by dosage, calculated by $AUC_{0-t}$, the compound of formula (I) obtained in Example 1 has an absolute bioavailability of ig of 0.95%, and the absolute bioavailability of ig of Form A was 8.75%, and the absolute bioavailability of ig of Form B was 8.76%, and the absolute bioavailability of ig of Form C was 5.17%.

Example 13

Tumor-inhibitory Effect on the Human Epidermatoid Squamous Cancer A431 Transplanted to the BALB/cA Nude Mouse A well-developed solid tumor A431 was selected and cut into several uniform bits of a size of 2-3 mm under sterile conditions, with one bit being inoculated subcutaneously to the right armpit of each of the BALB/cA nude mice using trocar. 7 days after inoculation, the mice were grouped randomly and were intragastrically administrated through mouth for 13 days continuously. The long axis (a) and the short axis (b) of the tumors were measured with a vernier caliper every 4 days. According to the formula V=ab²/2, the tumor volume (mm³) could be calculated. The tested animals were neck-off killed 23 days after the inoculation, and anatomized to obtain the tumors. The tumors were weighed, and the tumor inhibition rate was calculated.

The results are shown in the table below, which indicate that Form A of p-toluenesulfonate of the compound of formula (I) has the significant inhibitory effect on the tumor,

| Groups | Dosage (mg/kg) | Administration route | Number of animals Start | Number of animals End | Weight of animals (g) (without tumor) | Weight of tumors (g) $\bar{x} \pm SD$ | Tumor inhibition rate % |
|---|---|---|---|---|---|---|---|
| Solvent control | 25 mL/kg | ig | 7 | 7 | 22.40 ± 2.81 | 1.13 ± 0.18 | 0 |
| Form A | 25 | ig | 5 | 5 | 21.58 ± 2.18 | 0.79 ± 0.20 | 29.99 |
|  | 50 | ig | 5 | 5 | 22.87 ± 3.96 | 0.69 ± 0.17 | 38.67 |
|  | 100 | ig | 5 | 5 | 22.13 ± 1.83 | 0.64 ± 0.23 | 43.63 |

Tumor-inhibitory Effect on the Human Ovarian Cancer SKOV-3 Transplanted to the BALB/cA Nude Mouse A tumor SKOV-3 in vigorous growth period was selected and cut into several uniform bits of a size of about 1.5 mm$^3$, which was inoculated subcutaneously to the right armpit of the BALB/cA nude mice using trocar under sterile conditions. The diameters of the transplanted tumors of nude mice were measured with a vernier caliper. The animals were grouped randomly when the tumors grew to a size of 80-100 mm$^3$. The tested animal group were intragastrically administrated through mouth as mentioned above once a day for 3 weeks continuously. The positive control drug MMC (Mitomycin) was intravenously administered once on the first day with a dose of 5 mg/kg. The negative control group were administered with 0.5% CMC—Na (Carboxymethyl Cellulose Sodium) with a dose of 0.2 mL/per mouse. The long axis (a) and the short axis (b) of the tumors were measured twice every week and the nude mice were weighed at the same time. According to the formula V=ab$^2$/2, the tumor volume (mm$^3$) could be calculated, based on which the relative tumor volume (RTV) was calculated (Calculation Formula: RTV=V$_t$/V$_0$, wherein V$_0$ represents the tumor volume measured at the grouping time of administration, and V$_t$ represents the tumor volume measured each time). The relative tumor proliferation rate T/C (%) was chosen as the index to evaluate the antitumor activity, which can be calculated according to the following formula:

$$T/C(\%) = (T_{RTV}/C_{RTV}) \times 100$$

$T_{RTV}$: RTV of the treated group; $C_{RTV}$: RTV of the negative control group The standard for evaluating the effectiveness: T/C (%)>60% means ineffective and T/C (%)≦60% means effective.

The results are shown in the table below, which indicate that Form A of p-toluenesulfonate of the compound of formula (I) has the significant tumor inhibitory effect.

According to the experimental method mentioned above, the tumor-bearing nude mice, into which the human ovarian cancer SKOV-3, the human lung cancer Calu-3, and the human lung cancer A549 were transplanted respectively, were intragastrically administrated with Form B (100 mg/kg) of the present invention through mouth twice a day for 3 weeks continuously. The relative tumor proliferation rate T/C as obtained was 28.5%, 35.1% and 56.3%, respectively.

According to the experimental method mentioned above, the tumor-bearing nude mice, into which the human ovarian cancer SKOV-3, the human lung cancer Calu-3, and the human lung cancer A549 were transplanted respectively, were intragastrically administrated with Form C (100 mg/kg) of the present invention through mouth twice a day for 3 weeks continuously. The relative tumor proliferation rate T/C as obtained was 23.2%, 39.4% and 58.7%, respectively.

The Form B and Form C of the p-toluenesulfonate of the compound of formula (I) were indicated to also have the significant tumor inhibitory effects.

Example 14

Toxicity Test of Long-term Administration 80 healthy SD rats, male and weighed 200~250 g, were grouped into 16 groups randomly, and were each intragastrically administered with Form A, B or C of the p-toluenesulfonate of the compound of formula (I) or a blank solvent (Five test groups with the dose of 20, 50, 100, 500 or 800 mg/(kg·day) and a solvent control group were set). The results after four weeks of the continuous administration indicated that: the rats administered with the dose of 20, 50, 100, 500 or 800 mg/(kg·day) of Form A, B or C respectively showed no abnormality in physical signs, appearance, behaviors, activities or shape of dejecta, and had a normal food intake, and the weight and weight increase of the rats were basically similar to the solvent control group without the statistical difference.

| Groups | Dosage, Administration route | | Number of animals Start | Number of animals End | Volume of tumor (mm$^3$) V$_0$ | Volume of tumor (mm$^3$) V$_{21}$ | RTV | T/C (%) |
|---|---|---|---|---|---|---|---|---|
| 0.5% CMC-Na | 0.2 mL/per mouse | ig | 12 | 12 | 85 ± 35 | 638 ± 339 | 9.6 ± 5.4 |  |
| MMC | 5 mg/kg | iv | 6 | 6 | 83 ± 13 | 258 ± 77 | 3.1 ± 0.5 | 32.0 |
| Form A | 200 mg/kg | ig | 6 | 6 | 86 ± 13 | 303 ± 72 | 3.5 ± 0.8 | 36.9 |
|  | 100 mg/kg | ig | 6 | 6 | 87 ± 41 | 345 ± 88 | 4.3 ± 1.3 | 45.0 |
|  | 50 mg/kg | ig | 6 | 6 | 79 ± 28 | 421 ± 89 | 5.1 ± 1.7 | 53.0 |

V$_0$ represents the tumor volume before the administration, and
V$_{21}$ represents the tumor volume after 3 weeks of continuous administration.

The inspection results of hematology, blood biochemistry, cardiogram, body temperature and urine showed that the various inspection indexes were similar to those of the control group and all varied in the normal ranges, indicating that the polymorphic forms of p-toluenesulfonate of the compound of formula (I) possessed low toxicity and high safety of administration.

Example 15

Pharmaceutical Composition

The capsules containing the p-toluenesulfonate of N-{4-[3-chloro-4-(3-fluoro-benzyloxy)phenylamino]-quinazolin-6-yl}-acrylamide were prepared from the following components:

| | | |
|---|---|---|
| | Form A | 15 g |
| | Starch | 15 g |
| | Lactose | 30 g |
| | PVPP | 2.5 g |
| | PVP | 2.5 g |
| | Talcum powder | 3 g |
| | Sodium dodecyl sulfate | 4 g |

According to the conventional method, Form A of the p-toluenesulfonate of N-{4-[3-chloro-4-(3-fluoro-benzyloxy)phenylamino]-quinazolin-6-yl}-acrylamide and starch were mixed and sieved, and then evenly mixed with other components mentioned above, and filled into common gelatin capsules.

Example 16

Pharmaceutical Composition

The tablets containing the p-toluenesulfonate of N-{4-[3-chloro-4-(3-fluoro-benzyloxy)phenylamino]-quinazolin-6-yl}-acrylamide were prepared from the following components:

| | | |
|---|---|---|
| | Form B | 20 g |
| | Starch | 20 g |
| | Lactose | 40 g |
| | PVPP | 3 g |
| | PVP | 3 g |
| | Talcum powder | 1.6 g |
| | Sodium dodecyl sulfate | 5 g |

According to the conventional method, Form B of p-toluenesulfonate of N-{4-[3-chloro-4-(3-fluoro-benzyloxy)phenylamino]-quinazolin-6-yl}-acrylamide and starch were mixed and sieved, and then evenly mixed with other components mentioned above, and pressed into tablets directly.

All documents referred to throughout this application are hereby fully incorporated by reference herein, just as each of them is individually cited to be incorporated into this application. Further, it would be appreciated that, after reading the above contents of the present invention, the skilled person in the art may make various changes or modifications to the invention without violating the spirit of the present invention, and these forms of changes would also fall within the scope defined in the claims of the application.

The invention claimed is:

1. A crystalline form A of p-toluenesulfonate salt of the N-{4-[3-chloro-4-(3-fluoro-benzyloxy) phenylamino]-quinazolin-6-yl}-acrylamide, wherein the X-ray powder diffraction pattern of the crystalline form A has peaks at the diffraction angle 2θ(°) of 5.92±0.10, 8.64±0.10, 11.86±0.10, 16.58±0.10, 16.94±0.10, 17.86 ±0.10, 19.12 ±0.10, 19.66±0.10, 20.12±0.10, 23.42±0.10, 24.14±0.10, 24.80±0.10, and 26.76±0.10.

2. The crystalline form of claim 1, wherein the X-ray powder diffraction pattern of the crystalline form A has peaks at the diffraction angle 2θ(°) of 9.80±0.10, 13.28±0.10, 14.78±0.10, 17.36±0.10, 18.62±0.10, 21.62±0.10, 22.12±0.10, 22.38±0.10, 23.14±0.10, 25.20±0.10, 27.24±0.10, 28.34±0.10, 28.78±0.10, 33.12±0.10, and 41.70±0.10.

3. The crystalline form of claim 1, wherein the X-ray powder diffraction pattern of the crystalline form A is substantially shown in FIG. 1.

4. The crystalline form of claim 1, wherein the infrared (IR) spectrum of the crystalline form A is substantially shown in FIG. 5.

5. A process for preparing a crystalline form A of p-toluenesulfonate salt of the N-{4-[3-chloro-4-(3-fluoro-benzyloxy) phenylamino]-quinazolin-6-yl}-acrylamide, comprising the steps of:
dissolving the compound of formula (I) in an organic solvent to form a solution;
dropwise adding a solution of p-toluenesulfonic acid in the organic solvent with stirring and controlling the molar ratio of the compound of formula (I) to p-toluenesulfonic acid in the range of 1:1 to 1:6, and
resulting in a crystalline precipitate, and filtering out and washing the crystal to obtain the desired crystalline form.

6. The process of claim 5, wherein the organic solvent is selected from the group consisting of tetrahydrofuran, methanol, ethanol, propanol, isopropanol, butanol, acetone, acetonitrile, DMSO, DMF, propanediol, and the mixtures thereof or the group consisting of tetrahydrofuran, methanol, ethanol, the mixture of tetrahydrofuran and methanol, and the mixture of tetrahydrofuran and ethanol.

7. The process of claim 5, wherein for step (b), the molar ratio of the compound of formula (I) to p-toluenesulfonic acid is in the range of 1:3 to 6.

8. The process according to claim 5, wherein the organic solvent is the mixture of tetrahydrofuran and methanol with a volume ratio of 1:1 to 3 or 1:2 to 3.

9. The process of claim 5, wherein the solution of the compound of formula (I) in the step (a) has a concentration of 3 to 8 g/100 mL or 4 to 6 g/100 mL.

10. The process of claim 5, wherein the solution of p-toluenesulfonic acid in the step (b) has a concentration of 10 to 30 g/100 mL or 15 to 25 g/100 mL.

11. The process of claim 5, wherein the solution of the compound of formula (I) in the step (a) has a concentration of 3 to 8 g/100 mL or 4 to 6 g/100 mL; the solution of p-toluenesulfonic acid in the step (b) has a concentration of 10 to 30 g/100 mL or 15 to 25 g/100 mL; and the organic solvent is the mixture of tetrahydrofuran and methanol with a volume ratio of 1:1 to 3 or 1:2 to 3.

12. A pharmaceutical composition comprising a crystalline form A of p-toluenesulfonate salt of the N-{4-[3-chloro-4-(3-fluoro-benzyloxy) phenylamino]-quinazolin-6-yl}-acrylamide and a pharmaceutically acceptable carrier.

* * * * *